United States Patent [19]

Lehmann

[11] 4,303,521
[45] Dec. 1, 1981

[54] COLUMN FOR THE TREATMENT OF A LIQUID BY MEANS OF A PARTICULATE MATERIAL

[75] Inventor: Hans-Dieter Lehmann, Hechingen, Fed. Rep. of Germany

[73] Assignee: Gambro Dialysatoren GmbH & Co KG, Fed. Rep. of Germany

[21] Appl. No.: 161,020

[22] Filed: Jun. 19, 1980

[30] Foreign Application Priority Data

Jul. 9, 1979 [SE] Sweden ................. 7905956

[51] Int. Cl.³ ............................................ B01D 29/08
[52] U.S. Cl. ................................... 210/282; 210/284
[58] Field of Search .................. 29/157.3 D, 157.3 V; 138/156, 157, 170, 171, 178, DIG. 11; 165/170; 210/232, 282, 284, 287, 336, 483, 497.01, 497.2

[56] References Cited

U.S. PATENT DOCUMENTS

| | | | |
|---|---|---|---|
| 1,590,120 | 6/1926 | Perry .................................. | 210/807 |
| 2,779,086 | 1/1957 | Rieppel et al. ..................... | 138/157 |
| 3,342,340 | 9/1967 | Shindell ............................. | 210/282 |
| 3,374,895 | 3/1968 | Krongos ............................. | 210/282 |
| 3,567,028 | 3/1971 | Nose .................................. | 210/232 |
| 3,984,324 | 10/1976 | Wang ................................. | 210/232 |

FOREIGN PATENT DOCUMENTS 408637 6/1979 Sweden .
411446 12/1979 Sweden .
1482071 8/1977 United Kingdom .

*Primary Examiner*—Ivars C. Cintins
*Attorney, Agent, or Firm*—Lerner, David, Littenberg & Samuel

[57] ABSTRACT

Columns for the treatment of a liquid with particulate material are disclosed comprising first and second layers of sheet material in face-to-face contact with each other, an inlet and an outlet located at points between the layers, and welds or the like for joining the layers together along a pair of substantially parallel paths between the inlet and the outlet in order to form an elongated space adapted to be filled with particulate material therebetween. In a preferred embodiment, the aforesaid column comprises a first column portion, and the column includes a second column portion which also includes layers of sheet material in face-to-face contact with each other, an inlet, an outlet, welds for joining the two layers of sheet material together along a pair of substantially parallel paths between the inlet and the outlet so as to form an elongated space adapted to be filled with the particulate material therebetween, and a tubular connector for connecting the outlet from the first column portion with the inlet to the second column portion so that liquid may be fed from the inlet to the first column portion through both column portions to the outlet from the second column portion for contact with the particulate material in both column portions.

18 Claims, 6 Drawing Figures

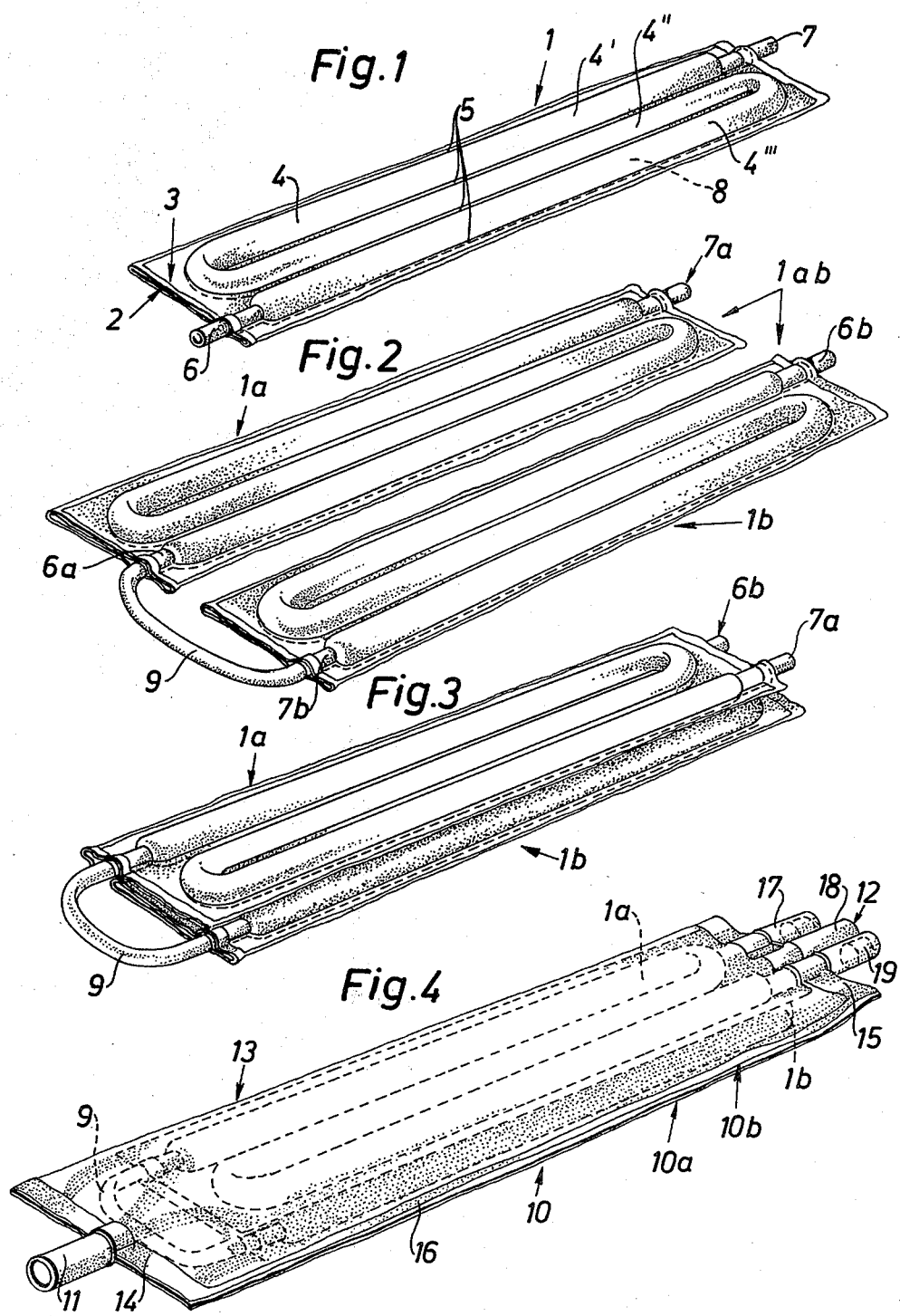

COLUMN FOR THE TREATMENT OF A LIQUID BY MEANS OF A PARTICULATE MATERIAL

FIELD OF THE INVENTION

The present invention relates to a column for the treatment of a liquid by means of a particulate material. More particularly, the present invention relates to such a column including an inlet and an outlet for the liquid, and an elongated space filled with the particulate material therebetween.

BACKGROUND OF THE INVENTION

Columns for the treatment of liquids by means of particulate material may be used, for example, for the removal of waste metabolites, and particularly nitrogenous poisons, from solutions containing such metabolites. An example of such a process in which activated carbon is used as the particulate material, is described in detail in U.S. Patent Application Ser. No. 104,446 filed on Dec. 17, 1979.

Such columns are usable in particular for the removal of waste metabolites, such as urea, from a hemofiltrate or the like from patients who suffer from uremia. The columns may also be used for the treatment of a variety of other liquids.

These columns are usually manufactured as a rigid outer casing enclosing the particulate material between two filters. An example of such a column is described in British Pat. No. 1,482,071.

With regard to background art, reference is also made to the above-mentioned U.S. Patent Application No. 104,446, which describes a process for which the unit in accordance with the present invention is particularly appropriate.

SUMMARY OF THE INVENTION

In accordance with the present invention, a column for treating a liquid with particulate material has been dicovered which comprises first and second layers of sheet material in face-to-face contact with each other, an inlet located at a first point between the first and second layers of sheet material, an outlet located at a second point between the first and second layers of sheet materials, and joining means for joining the first and second layers of sheet material together along a pair of substantially parallel paths between the inlet and the outlet sized to form an elongated space adapted to be filled with the particulate material therebetween so that the liquid may be fed from the inlet to the outlet for contact with the particulate material. By producing a column in this manner and by forming the elongated space to be filled with the particulate material by placing two sheets flat against each other and joining them together on either side of the elongated space along two substantially parallel curved paths, it is possible in an inexpensive and effective manner to obtain great freedom from the optional shaping of the elongated space for the particulate material. In particular, this space can thus be chosen to have great length in relation to its transverse dimension. For example, the length may be chosen to be 100 to 200 times greater than the diameter if the space is made substantially circular cylindrical.

The elongated space is thus preferably divided into substantially parallel sub-spaces, and in this manner the space can be made relatively long while retaining limiting outer dimensions. It is thus possible for example to make the spaces substantially S-shaped.

In a preferred embodiment of the column of the present invention, the substantially parallel paths formed between the inlet and the outlet forms a sinuous elongated space therebetween.

In a preferred embodiment of the column of the present invention, the first and second layers of sheet material discussed above form a first column portion, and third and fourth layers of sheet material in face-to-face contact with each other form a second column portion. The second column portion thus also includes a second inlet located at a first point between the third and fourth layers of sheet material, and a second outlet located at a second point between the third and fourth layers of sheet material, second joining means for joining the third and fourth layers of sheet material together in the same manner as the first and second layers of sheet material as discussed above, and connecting means for connecting the first outlet to the second inlet whereby liquid may be fed from the first inlet through the first and second column portions to the second outlet for contact with particulate material in both column portions therebetween.

In this manner a double column is formed, and in a preferred embodiment the sub-spaces included therein may be arranged to be three-dimensional. For example, two substantially planar columns can be placed on top of one another and it is therefore possible for limited outer dimensions to be maintained, even though the total length of the space holding the particulate material is relatively substantial. Such a column holding 180 grams (dry) of activated carbon may be designed for example so that it has a useful treatment length of 200 cm. within a total space of approximately $33 \times 6 \times 5$ cm.

In another embodiment of the present invention, the double columns include an outer casing for enclosing the first and second column portions therewithin, and preferably wherein the first and second column portions are located in juxtaposed, substantially parallel planes with respect to each other. When such a double column is employed enclosed within a joint outer casing the column obtained is particularly appropriate for use in the method described in the afore-mentioned U.S. Patent Application Serial No. 104,446, for removing waste metabolites by alternating heating and cooling of a column of activated carbon. Thus, the outer casing may be alternately filled with hot or cold liquid and the liquid so treated may be flushed through the inner columns during the cold periods, while the columns can instead be counter-flushed by cleaning liquid during the hot periods. These hot and cold liquids may be fed and withdrawn respectively through inlets and outlets for these treatment media for supply to the outer casing.

In a preferred embodiment of this aspect of the present invention, the outer casing employed comprises a pair of sheet portions, and includes outer casing joining means for joining the outer peripheries of the pair of sheet portions to each other so as to form a closed space for enclosing the first and second column portions therebetween. Preferably, weldable sheets are used so that the joining can be achieved by means of welding.

In another embodiment of the column of the present invention, a particularly dimensionally stable and simple unit includes inlets and outlets for the first and second column portions prepared from pipes or flexible tubing welded between the respective sheets of the first and second column portions, and furthermore wherein the inlet for the first column portion and the outlet for the second column portion are welded between the sheet portions of the joint outer casing for the first and second column portions.

In a preferred embodiment of this aspect of the present invention, the double column further includes a substantially dimensionally stable external casing which is preferably thermally insulating and which can also serve as a transport package, particularly in the embodiment where the outer casing is to be filled alternately with hot and cold liquids.

In another embodiment of the present invention, filter members are included in the inlets and outlets for the columns or column portions in order to allow liquid to pass therethrough but to retain the particulate material therebetween.

The columns in accordance with the present invention are preferably made of a tubular material welded together on either side of the elongated space along two substantially parallel curved tracks, wherein the welding also takes place appropriately along the longitudinal lateral edges closed on flattening and as a result the width of the sub-spaces enclosed can be maintained more accurately irrespective of whether the tubular material enters the welding tool somewhat obliquely.

BRIEF DESCRIPTION OF THE DRAWINGS

The invention will now be described in greater detail, with reference to the enclosed drawings, which show different preferred modes of carrying out the subject of the invention and, in which:

FIG. 1 is a front perspective view of an embodiment of the present invention;

FIG. 2 is a front perspective view of two columns of the type shown in FIG. 1 coupled together in a series, to form a double column in accordance with the present invention;

FIG. 3 is a front perspective view of the double column in accordance with FIG. 2 folded together to a more compact unit;

FIG. 4 is a front perspective view of the double column in accordance with FIG. 3 enclosed in an outer casing;

DETAILED DESCRIPTION

Figure 5:
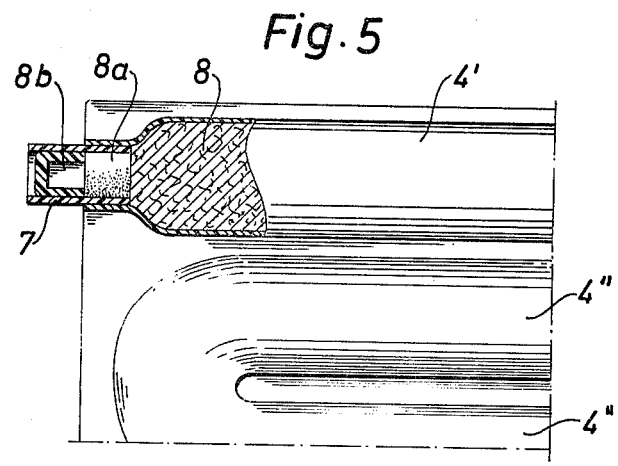
FIG. 5 is a top, partial, partially sectional view of an inlet or outlet for a column in accordance with the present invention.

Referring to the Figures, in which like numerals refer to like portions thereof, FIG. 1 shows a preferred mode of a column in accordance with this invention. The column as a whole is designated by the numeral 1. In this example, the column is made up of a bottom sheet 2 and a top sheet 3 placed flat against one another. These sheets may be separate sheets welded together, but it is preferred that they are constituted of a single piece of tubular material. In the example shown, a substantially S-shaped elongated space 4 is present between the sheets 2 and 3, and this elongated space 4 is produced by welding together substantially parallel curved tracks. This weld as a whole is designated by the numeral 5. At the same time as weld 5 is produced, pipes 6 and 7 are also welded between the two sheets, 2 and 3. These pipes are intended to serve as an inlet and an outlet, respectively, for the liquid to be treated i.e., with a particulate activated material such as activated carbon, which after the welding together of the sheets 2 and 3 is made to fill the elongated space 4. This elongated space 4 is, by virtue of its S-shape, divided into sub-spaces 4', 4" and 4'''.

Inlet 7 and surrounding portions of the column are shown on a larger scale in FIG. 5, which illustrates how the inlet can be provided with a filter 8a and a closing plug 8b. The other inlets and outlets can, of course, be produced in a like manner.

The filling of the column takes place appropriately in such a manner that the particles, e.g. circular cylindrical rods of activated carbon, 3–5 mm. long, are flushed in together with a liquid such as isotonic salt solution (0.9% NaCl).

BEST MODE OF CARRYING OUT THE INVENTION

FIGS. 2–4 and 6 show the best mode of carrying out the invention. Accordingly, two columns 1a and 1b are coupled in a series to form a double column, which is designated as a whole by numeral 1ab. Outlet 6a of the single column 1a is coupled by means of flexible tubing 9 to the inlet 7b of the single column 1b. Pipe 7a serves as an inlet to the unit as a whole, and the pipe 6b, in a similar manner, serves as an outlet from the unit as a whole.

FIG. 3 shows how the two single columns 1a and 1b can be folded together to form a more compact unit. FIG. 4 shows how this compact unit can be enclosed in a joint outer casing 10 which comprises an inlet 11 and an outlet 12. Inlet 11 and outlet 12 are formed by pipes which are welded between two sheets 10a and 10b placed substantially flat against one another. In the example shown, these sheets are formed by a single piece of sheet which is doubled over along edge 13. In practice, however, wholly separate sheets may also be used, which are then welded together along edge 13 as well as along the end welds 14 and 15 and along the longitudinal weld 16. Numerals 17, 18 and 19 designate caps by means of which pipe 12, inlet 7a and outlet 6b can be closed. The pipe 11 can, of course, also be closed by a corresponding cap.

Figure 6:
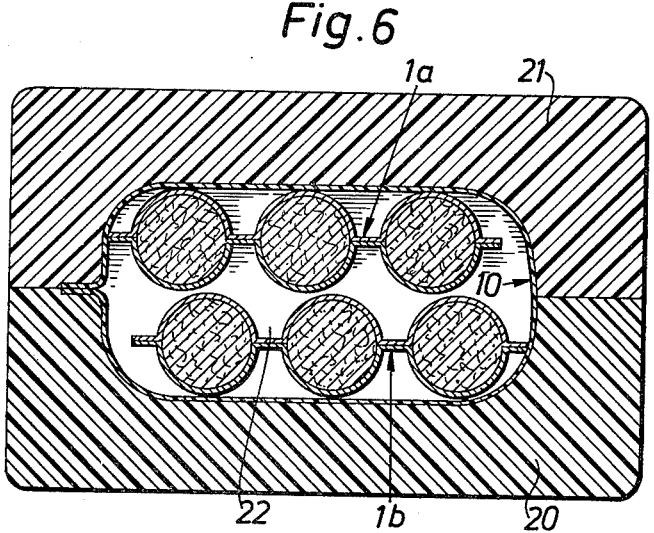
FIG. 6 is a side, sectional view of a double column in accordance with FIG. 4 arranged inside a substantially dimensionally stable and preferably thermally insulated external casing.

FIG. 6 illustrates how the double column in accordance with FIG. 4 may be enclosed in a substantially dimensionally stable and preferably thermally insulated external casing, whose halves are designated 20 and 21, respectively. This is particularly suitable if space 22 within outer casing 10 is intended to be filled with a hot liquid under pressure. In such a case there would be a risk that without the external casing the unit might swell up and possibly crack.

A preferred field of the application of the present invention is for the removal of waste metabolites, especially nitrogenous poisons such as urea, from hemofiltrate or dialysis solutions from a patient who suffers from uremia. In the case of hemofiltrate, the same is conducted at a rate of approximately 100 ml/minute, preferably through three columns each of which may be of a design in accordance with FIG. 4, and be filled with activated carbon. While one column is continuously cooled, as described in detail in the above-mentioned patent application, the two others may be adapted so that they are alternately cooled and heated for absorption and desorption, respectively.

However, it will be clear to a person skilled in this art, that the column in accordance with this invention can also be used for other purposes, the contents of the elongated space 4 being dependent upon the liquid which is to be treated and upon the treatment that is desired. In place of activated carbon, various other adsorbents can be used and in addition various ion-exchanging materials may also be considered for their action upon the liquid so treated.

I claim:

1. A column for treating a liquid with particulate material which comprises first and second layers of sheet material in face-to-face contact with each other, an inlet located at a first point between said first and second layers of sheet material, an outlet located at a second point between said first and second layers of sheet material, joining means for joining said first and second layers of sheet material together in a substantially flat plane and along a pair of substantially parallel paths between said inlet and said outlet so as to form a substantially planar elongated space therebetween, and particulate material contained within said elongated space whereby said liquid may be fed from said inlet to said outlet for contact with said particulate material therebetween.

2. The column of claim 1, wherein said substantially parallel paths form a sinuous elongated space between said inlet and said outlet.

3. The column of claim 2, wherein said sinuous elongated space comprises a plurality of mutual parallel legs.

4. The column of claim 2, wherein said sinuous elongated space is substantially S-shaped.

5. The column of claim 1, wherein said first and second layers of sheet material comprise a first column portion, said joining means comprises first joining means, said inlet comprises a first inlet, and said outlet comprises a first outlet, and including a second column portion comprising third and fourth layers of sheet material in face-to-face contact with each other, a second inlet located at a first point between said third and fourth layers of sheet material, a second outlet located at a second point between said third and fourth layers of sheet material, second joining means for joining said second and third layers of sheet material together in a substantially flat plane and along a pair of substantially parallel paths between said second inlet and said second outlet so as to form a substantially planar elongated space therebetween, particulate material contained within said elongated space, and connecting means for connecting said first outlet to said second inlet whereby said liquid may be fed from said first inlet through said first and second column portions to said second outlet for contact with said particulate material therebetween.

6. The column of claim 5 including outer casing means for enclosing said first and second column portions therewith.

7. The column of claim 5 or 6, wherein said first and second column portions are located in juxtaposed substantially parallel planes.

8. The column of claim 6 including an outer casing inlet and an outer casing outlet whereby a treatment medium may be supplied to and withdrawn from said outer casing so as to contact said first and second column sections therein.

9. The column of claim 6 or 8, wherein said outer casing comprises a pair of sheet portions in face-to-face contact with each other so as to form a closed space for enclosing said first and second column portions therebetween.

10. The column of claim 6 including external casing means comprising a substantially dimensionally stable and thermally insulating casing for enclosing said outer casing means therein.

11. The column of claim 5, wherein said inlet, said outlet, and said connecting means comprise flexible tubes.

12. The column of claim 1 or 5, wherein said inlets and said outlets include filter means for retaining said particulate material within said elongated space while permitting liquid to flow therethrough.

13. The column of claim 1, wherein said inlet and said outlet comprise flexible tubes.

14. The column of claim 13 or 11, wherein said flexible tubes are welded between said layers of sheet material.

15. The column of claim 1, wherein said first and second layers of sheet material are formed from a tubular sheet of material welded together along its longitudinal edge produced by flattening said tubular sheet of material.

16. The column of claim 1 wherein said particulate material comprises an adsorbent.

17. The column of claim 1 wherein said particulate material comprises an ion exchange material.

18. The column of claim 1 wherein said particulate material comprises activated carbon.

* * * * *